US006919214B2

United States Patent
Kim et al.

(10) Patent No.: US 6,919,214 B2
(45) Date of Patent: Jul. 19, 2005

(54) APPARATUS FOR ANALYZING A SUBSTRATE EMPLOYING A COPPER DECORATION

(75) Inventors: Gi-Jung Kim, Yongin (KR);
Kyoo-Chul Cho, Yongin (KR);
Tae-Yeol Heo, Yong (KR); Sook-Hyun Park, Suwon (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 84 days.

(21) Appl. No.: 10/688,954

(22) Filed: Oct. 21, 2003

(65) Prior Publication Data

US 2004/0112742 A1 Jun. 17, 2004

(30) Foreign Application Priority Data

Dec. 11, 2002 (KR) ................................ 10-2002-0078726

(51) Int. Cl.[7] .............................................. H01L 21/00
(52) U.S. Cl. .......................... 438/14; 438/687; 205/118
(58) Field of Search .......................... 438/14, 441, 687

(56) References Cited

U.S. PATENT DOCUMENTS

| | | | | |
|---|---|---|---|---|
| 4,399,020 A | * | 8/1983 | Branchick et al. | 204/269 |
| 5,980,720 A | * | 11/1999 | Park et al. | 205/118 |
| 6,773,573 B2 | * | 8/2004 | Gabe et al. | 205/296 |
| 2001/0016420 A1 | * | 8/2001 | Chou | 438/687 |

FOREIGN PATENT DOCUMENTS

KR        1001899940000        1/1990

OTHER PUBLICATIONS

Shin et al. "Influence of Cu–decoration to Individual Crystal Originated Pits on Si Wafer", Japanese Journal of Applied Physics, vol. 42, pp. 4187–4192, Jul. 2003.*

Itsumi et al., "Gate Oxide Defects in MOSLISIs and Octahedral Void Defects in Czochralski Silicon" Japanes Journal of Applied Physics, vol. 37, pp 1228–1235, Mar. 1998.*

Park et al., "Nature of Surface and Bulk Defect Induced by Low Dose Oxygeng Implantation in Separation by Implanted Oxygen Wafers", Japanese Journal of Applied Physics, vol., 40, pp. 2178–2185, Apr. 2001.*

* cited by examiner

*Primary Examiner*—W. David Coleman
(74) *Attorney, Agent, or Firm*—Lee & Morse, P.C.

(57) ABSTRACT

An apparatus for analyzing a substrate employing a copper decoration includes a bath having at least two receiving containers for receiving electrolytes, slots formed at insides of the receiving containers for receiving substrates to be analyzed in a direction that is normal to a bottom face of the bath, lower copper plates provided in the receiving containers, the lower copper plates making contact with entire rear faces of the substrates received in the receiving containers, upper copper plates provided in the receiving containers, each of the upper copper plates corresponding to a respective one of the lower copper plates, and separated from front faces of the substrates, and a power source connected to the upper copper plates and the lower copper plates for providing voltages to the same. A plurality of substrates may be simultaneously analyzed using one apparatus thereby greatly reducing an amount of time required for the analysis.

19 Claims, 7 Drawing Sheets

APPARATUS FOR ANALYZING A SUBSTRATE EMPLOYING A COPPER DECORATION

BACKGROUND OF THE INVENTION

1. Field of the Invention

The present invention relates to an apparatus for analyzing a substrate employing a copper decoration. More particularly, the present invention relates to an apparatus for analyzing a substrate employing a copper decoration for analyzing a crystalline defect existing in a silicon wafer.

2. Description of the Related Art

As semiconductor devices become more highly integrated, the quality of silicon wafers used as substrates for the semiconductor devices has a greater effect on manufacturing yield of the semiconductor devices and reliability of the semiconductor devices. The quality of a silicon wafer may be determined by a distribution and density of defects generated in the silicon wafer and on a surface of the silicon wafer during a process for manufacturing the silicon wafer.

Generally, in silicon wafer manufacturing technology, after a poly-crystalline silicon ingot is provided, a single crystalline silicon ingot is manufactured using a Czochoralski crystal growth process or a float zone crystal growth process. The single crystalline silicon ingot is cut to form a thin silicon wafer. After one face of the thin silicon wafer is polished, the polished silicon wafer is cleaned to complete the silicon wafer for the semiconductor devices.

When the silicon wafer is manufactured employing the above-described method, crystalline defects such as D-defects, crystal original particles (COP) and oxygen extractions are frequently generated on the silicon wafer or in the silicon wafer. When an oxide film is formed on the silicon wafer having the crystalline defects, the oxide film may have a poor characteristic at portions of the silicon wafer where the crystalline defects are generated. Particularly, the crystalline defects may cause failures of a gate oxide film and a shallow trench isolation (STI) of a semiconductor device.

To prevent the above-mentioned failures, a method for rapidly and precisely analyzing defects generated in or on the silicon wafer is important. Methods for analyzing defects of a silicon wafer include a method for analyzing a silicon wafer using a particle measurement apparatus, a method for analyzing a silicon wafer using an etching apparatus, a method for analyzing a silicon wafer using a laser scattering particle counter, and a method for analyzing a silicon wafer employing a destruction of an oxide film through manufacturing a metal oxide semiconductor (MOS) device. However, each of these methods may have respective disadvantages. In particular, with the method using the particle measurement apparatus, only defects having very small dimensions, of below about 0.12 $\mu$m, can be found at a portion of a silicon wafer. Although defects generated in the silicon wafer may be measured by the methods using the etching apparatus and the laser scattering particle counter, original shapes of the defects may be destructed by using these methods. Additionally, although defects generated in a silicon wafer may be analyzed by an effect thereof to an oxide film in the method employing the destruction of the oxide film through manufacturing a MOS device, it is very difficult to analyze morphologies of the defects by this method.

Recently, a copper decoration method for analyzing defects of a silicon wafer has been developed in an effort to overcome the above-mentioned problems. In the copper decoration method, after a silicon oxide film is formed on a silicon wafer, an electric field is applied to both ends of the silicon wafer so that copper ions are adsorbed at portions of the silicon wafer where defects are generated.

Figure 1:
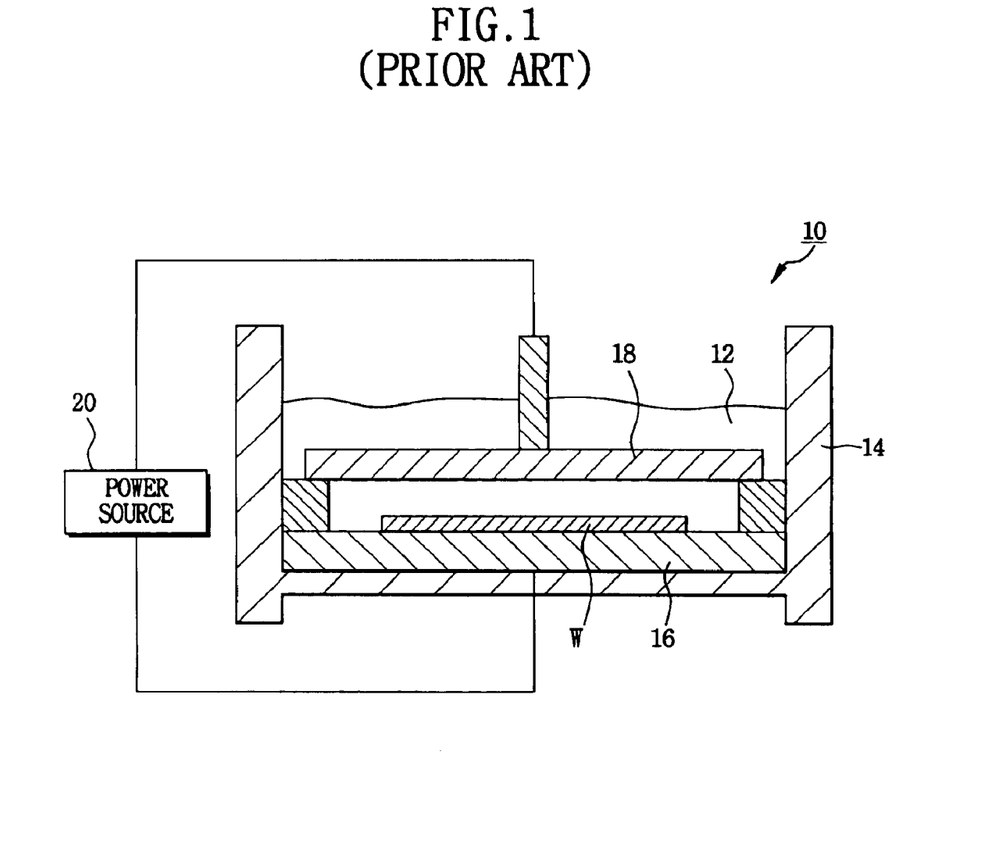
FIG. 1 illustrates a schematic cross-sectional view of a conventional copper decoration apparatus for analyzing a substrate.

FIG. 1 illustrates a schematic cross-sectional view of a conventional copper decoration apparatus for analyzing a substrate.

Referring to FIG. 1, a conventional copper decoration apparatus 10 has a bath 14, a lower copper plate 16, an upper copper plate 18 and a power source 20.

The bath receives an electrolyte 12. The lower copper plate 16 is placed on a bottom face of the bath 14. A rear face of a silicon wafer W to be analyzed is placed on the lower copper plate 16. The upper copper plate 18 corresponds to the lower copper plate 16, and is separated from the lower copper plate 16. The power source 20 applies voltages to the upper and lower copper plates 16 and 18.

With the above-described conventional apparatus 10, one silicon wafer W is analyzed through one process for analyzing a defect of the silicon wafer W. Including preparatory processes for analysis, about one hour is required to analyze one silicon wafer W. Thus, the time required for analyzing several silicon wafers may be greatly increased when a plurality of silicon wafers are analyzed using the conventional copper decoration apparatus 10. Also, a method for analyzing silicon wafers may be complicated because each wafer should undergo several hours worth of preparatory processes prior to being analyzed.

SUMMARY OF THE INVENTION

In an effort to overcome the problems described above, the present invention provides an apparatus for analyzing a substrate employing a copper decoration capable of analyzing a plurality of substrates simultaneously.

In accordance with an embodiment of the present invention, there is provided an apparatus for analyzing a substrate employing a copper decoration, the apparatus including a bath having at least two receiving containers for receiving electrolytes, slots formed at insides of the receiving containers for receiving substrates to be analyzed in a direction that is normal to a bottom face of the bath, lower copper plates provided in the receiving containers, the lower copper plates making contact with entire rear faces of the substrates received in the receiving containers, upper copper plates provided in the receiving containers, each of the upper copper plates corresponding to a respective one of the lower copper plates, and separated from front faces of the substrates, and a power source connected to the upper copper plates and to the lower copper plates for providing voltages to the upper copper plates and to the lower copper plates.

The receiving containers are preferably separated from each other to prevent the electrolytes received in the receiving containers from being mixed together. The apparatus as claimed in claim 1, wherein the upper copper plates and the lower copper plates provided in the receiving containers are preferably connected to the power source in parallel. First switching devices provided between the power source and the lower copper plates in order to selectively apply the voltages to the lower copper plate from the power source may be included in the apparatus. Further, second switching devices may be provided between the power source and the upper copper plates in order to selectively apply the voltages to the upper copper plates from the power source. Additional power sources corresponding to the number of the receiving containers, and the upper copper plates and the lower copper plates are preferably connected to each of the power sources in series. The power source preferably has a negative bias terminal connected to the lower copper plates, and a positive bias terminal connected to the upper copper plates. The lower copper plates preferably have connecting terminals connected to the power source. Similarly, the upper copper plates preferably have connecting terminals connected to the power source. The electrolyte preferably includes methanol. The receiving containers preferably have predetermined depths to completely receive the substrates in the direction that is normal to the bottom face of the bath.

In accordance with another feature of an embodiment of the present invention, there is provided an apparatus for analyzing a substrate employing a copper decoration, including a bath having at least two receiving containers defined by isolation walls wherein the receiving containers independently receive electrolytes, respectively, a lower copper plate provided on an entire bottom face of the bath, upper copper plates provided in the receiving containers, the upper copper plates corresponding to the lower copper plate and being separated from the lower copper plate and a power source connected to the upper copper plates and to the lower copper plate for providing voltages to the upper copper plates and to the lower copper plate.

The receiving containers preferably define portions of the lower copper plate so that the portions of the lower copper plate defined by the receiving containers have respective sizes sufficient to receive rear faces of substrates to be analyzed. Switching devices may be further provided between the power source and the upper copper plates in order to selectively apply the voltages to the upper copper plates from the power source. The lower copper plate preferably includes a connecting terminal connected to the power source. The upper copper plates preferably include connecting terminals connected to the power source. The power source preferably includes a negative bias terminal connected to the lower copper plate, and a positive bias terminal connected to the upper copper plates.

In accordance with another feature of an embodiment of the present invention, there is provided an apparatus for analyzing a substrate employing a copper decoration, including a bath including a bottom face for receiving at least two substrates to be analyzed, wherein an electrolyte is received in the bath, a lower copper plate provided on an entire bottom face of the bath wherein the substrates to be analyzed are placed on an upper face of the lower copper plate, an upper copper plate provided in the bath, the upper copper plate corresponding to the lower copper plate and being separated from the lower copper plate, and a power source for providing voltages to the upper copper plate and to the lower copper plate.

The power source preferably includes a negative bias terminal connected to the lower copper plate, and a positive bias terminal connected to the upper copper plate.

According to the present invention, a plurality of silicon wafers may be simultaneously analyzed using one apparatus for analyzing a substrate. Therefore, a time for analyzing the silicon wafers may be greatly reduced.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE PREFERRED EMBODIMENTS

Korean Patent Application No. 2002-78726, filed on Dec. 11, 2002, and entitled: "Apparatus For Analyzing A Substrate Employing A Copper Decoration," is incorporated by reference herein in its entirety.

The present invention will now be described more fully hereinafter with reference to the accompanying drawings, in which preferred embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, the thickness of layers and regions are exaggerated for clarity. Like numbers refer to like elements throughout.

Embodiment 1

Figure 2:
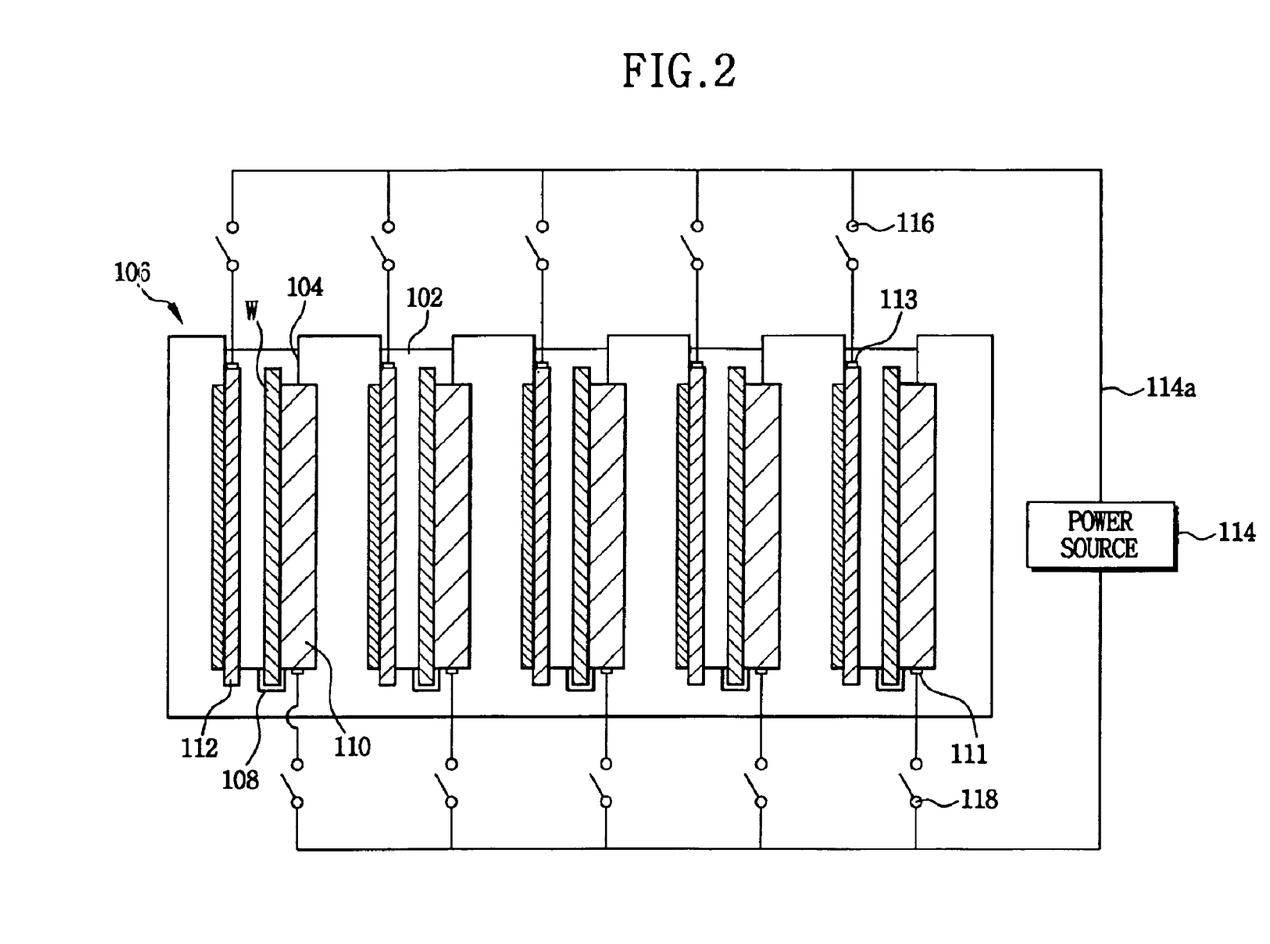
FIG. 2 illustrates a schematic cross-sectional view of an apparatus for analyzing a substrate employing a copper decoration according to a first embodiment of the present invention.
Figure 3:
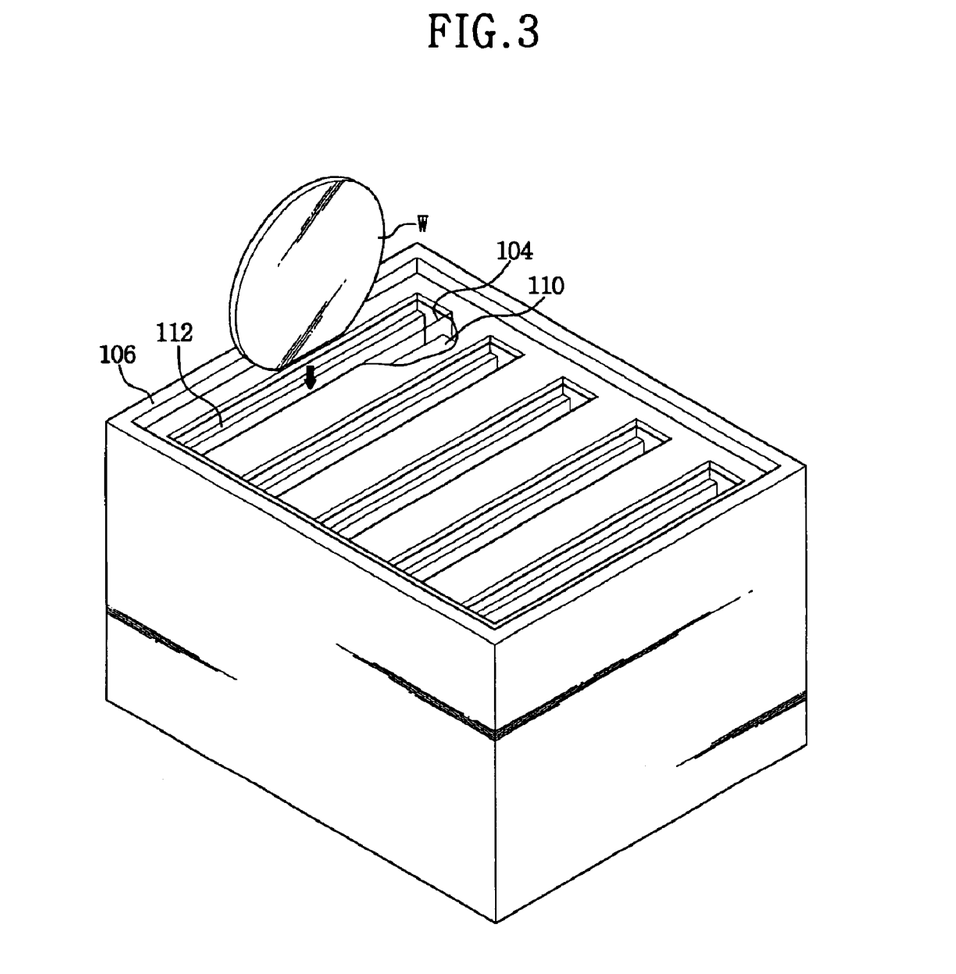
FIG. 3 illustrates a perspective view of the apparatus for analyzing a substrate employing a copper decoration according to the first embodiment of the present invention.

FIG. 2 illustrates a schematic cross-sectional view of an apparatus for analyzing a substrate employing a copper decoration according to a first embodiment of the present invention, and FIG. 3 illustrates a perspective view of the apparatus for analyzing a substrate employing the copper decoration according to the first embodiment of the present invention.

Referring to FIGS. 2 and 3, the apparatus for analyzing a substrate has a bath 106 including at least two receiving containers 104 for receiving electrolytes 102. The receiving containers 104 are separated from each other in order to prevent the electrolytes 102 received in the receiving containers 104 from being mixed together. Hereinafter, the bath 106 will be explained as having N numbers of receiving containers 104. Additionally, the receiving containers 104 will be referred to as a first receiving container to an N-th receiving container.

Silicon wafers W to be analyzed are inserted into the receiving containers 104 in a direction that is normal to a bottom face of the bath 106 so that lateral portions of the silicon wafers W make contact with bottom faces of the receiving containers 104. The receiving containers 104 have predetermined depths to completely receive the silicon wafers W to be analyzed. That is, the silicon wafers W to be analyzed are completely inserted into the receiving containers 104, respectively.

The electrolytes 102 received in the receiving containers 104 include methanol. Because the methanol has good solvency relative to copper ions, methanol is frequently utilized for a copper decoration apparatus. The silicon wafer W to be analyzed is formed by forming an oxide film on a bare silicon wafer manufactured using a process for forming a wafer. The oxide film on the bare silicon wafer includes silicon oxide and has a thickness of about 400 to about 1,200 Å. The bath 106 includes an insulation material such as a fluorine-containing resin.

The receiving containers 104 respectively include slots 108 formed therein for receiving the silicon wafers W in a direction that is normal to the bottom face of the bath 106. Each slot 108 supports an edge portion of a silicon wafer W to be analyzed. The slots 108 are provided to each receive one silicon wafer W to be analyzed in one receiving container 104.

First to N-th lower copper plates 110 are provided in the first to N-th receiving containers 104, respectively. The first to N-th lower copper plates 110 respectively make contact with entire rear faces of the silicon wafers W to be analyzed. Namely, the first lower copper plate 110 is installed in the first receiving container 104 to make contact with an entire rear face of the silicon wafer W to be analyzed that is inserted in the first receiving container 104. In addition, the N-th lower copper plate 110 is provided in the N-th receiving container 104 to make contact with an entire rear face of the silicon wafer W to be analyzed that is inserted in the N-th receiving container 104. Since the silicon wafers W to be analyzed are inserted into the receiving containers 104 in a direction that is normal to the bottom face of the bath 106, faces of the first to N-th lower copper plates 110, which make contact with the entire rear faces of the silicon wafers W, are positioned in the direction that is normal to the bottom face of the bath 106.

First to N-th upper copper plates 112 are provided in the first to N-th receiving containers 104, respectively. The first to N-th upper copper plates 112 are respectively separated from the first to N-th lower copper plates 110, and respectively correspond to the first to N-th lower copper plates 110. That is, the first upper copper plate 112 corresponding to the first lower copper plate 110 is installed in the first receiving container 104, and the N-th upper copper plate 112 corresponding to the N-th lower copper plate 110 is installed in the N-th receiving container 104. Here, intervals between the lower copper plates 110 and the upper copper plates 112 are maintained to respectively separate silicon wafers W to be analyzed from the upper copper plates 112 when the silicon wafers W to be analyzed are inserted in the receiving containers 104.

A power source 114 is provided to supply the upper and lower copper plates 112 and 110 with voltages, respectively. The power source 114 is connected to the upper and lower copper plates 112 and 110 so that predetermined electric fields are respectively generated between the upper copper plates 112 and the lower copper plates 110. The upper and lower copper plates 112 and 110 respectively have connecting terminals 111 and 113 for receiving the voltages from the power source 114. The power source 114 includes power cables 114a connected to the connecting terminals 111 and 113 of the upper and lower copper plates 112 and 110, respectively. Negative (−) bias voltages are applied to the lower copper plates 110 from the power source 114 while positive (+) bias voltages are applied to the upper copper plates 112 from the power source 114.

In the present embodiment, one power source 114 is provided, and then the first to N-th upper copper plates 112 and the first to N-th lower copper plates 110 are respectively connected in parallel to a positive bias terminal and a negative bias terminal of the power source 114. Namely, the power cables 114a extending from the positive bias terminal of the power source 114 are connected in parallel to the first to N-th upper copper plates 112. Meanwhile, the power cables 114a extending from the negative bias terminal of the power source 114 are connected in parallel to the first to N-th lower copper plates 110. First to N-th upper switching devices 116 are disposed between the power cables 114a and the first to N-th upper copper plates 112, respectively. Also, first to N-th lower switching devices 118 are disposed between the power cables 114a and the first to N-th lower copper plates 110, respectively. Therefore, the first to N-th upper switching devices 116 may be selectively operated to selectively apply the voltages to the first to N-th upper copper plates 112. Additionally, the first to N-th lower switching devices 118 may be selectively operated to selectively apply the voltages to the first to N-th lower copper plates 110.

As shown in FIG. 2, the apparatus for analyzing a substrate has all of the first to N-th upper switching devices 116 and all of the first to N-th lower switching devices 118. However, when one of the lower switching devices 118 corresponding to one of the upper switching devices 116 is OFF, the electric fields are not generated between the upper copper plates 112 and the lower copper plates 110 respectively connected to the upper switching devices 116 and lower switching devices 118. Therefore, the apparatus for analyzing a substrate may have the first to N-th upper switching devices 116 without the first to N-th lower switching devices 118. On the contrary, the apparatus for analyzing a substrate may have the first to N-th lower switching devices 118 without the first to N-th upper switching devices 116.

Figure 4:
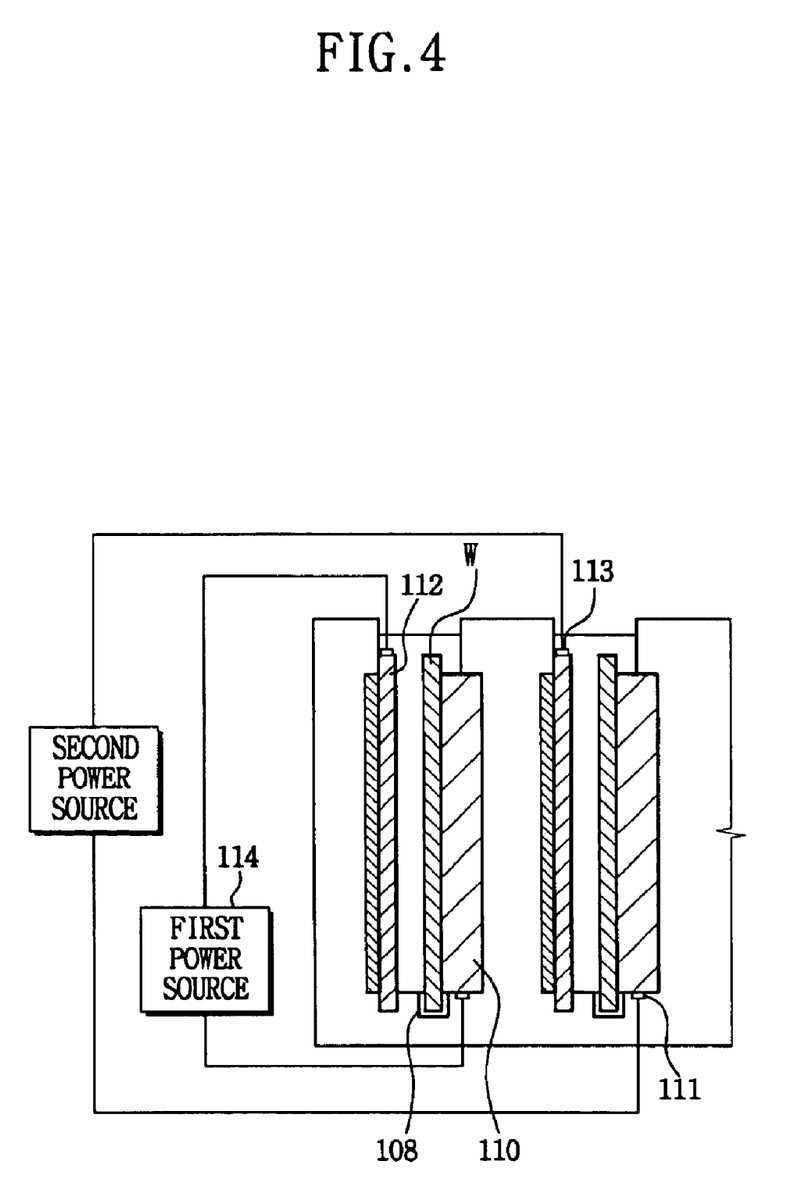
FIG. 4 illustrates a schematic cross-sectional view of an apparatus for analyzing a substrate according to another embodiment of the present invention.

FIG. 4 illustrates a schematic cross-sectional view of an apparatus for analyzing a substrate according to another embodiment of the present invention.

Referring to FIG. 4, an apparatus for analyzing a substrate includes a plurality of power sources 114 and a plurality of receiving containers 104. The number of power sources 114 corresponds to the number of receiving containers 104. Positive and negative terminals of the power sources 114 are respectively connected to upper copper plates 112 and lower copper plates 110 provided in series in the receiving containers 114. When first to N-th power sources 114 are provided, the first power source 114 is serially connected to a first upper copper plate 112 and to a first lower copper plate 110. Also, the N-th power sources 114 is connected to an N-th upper copper plate 112 and to an N-th lower copper plate 110 in series.

When the apparatus for analyzing a substrate having the above-described construction is employed, silicon wafers W to be analyzed are independently analyzed in related receiving containers 104, respectively, Thus, a plurality of silicon wafers W may be simultaneously analyzed using one apparatus for analyzing a substrate.

Additionally, dimensions of the receiving containers 104 in a direction that is parallel to a direction of a bottom face of the bath are greatly reduced because the receiving containers 104 receive the silicon wafers W to be analyzed in a direction that is vertical with respect to, or normal to, a bottom face of the bath. Hence, a number of receiving containers 104 in an apparatus for analyzing a substrate may be increased without necessarily increasing the size of the apparatus, or by increasing the size thereof only slightly.

Hereinafter, a method for analyzing silicon wafers by means of the apparatus described above that utilizes a copper decoration will be described.

Figure 5:
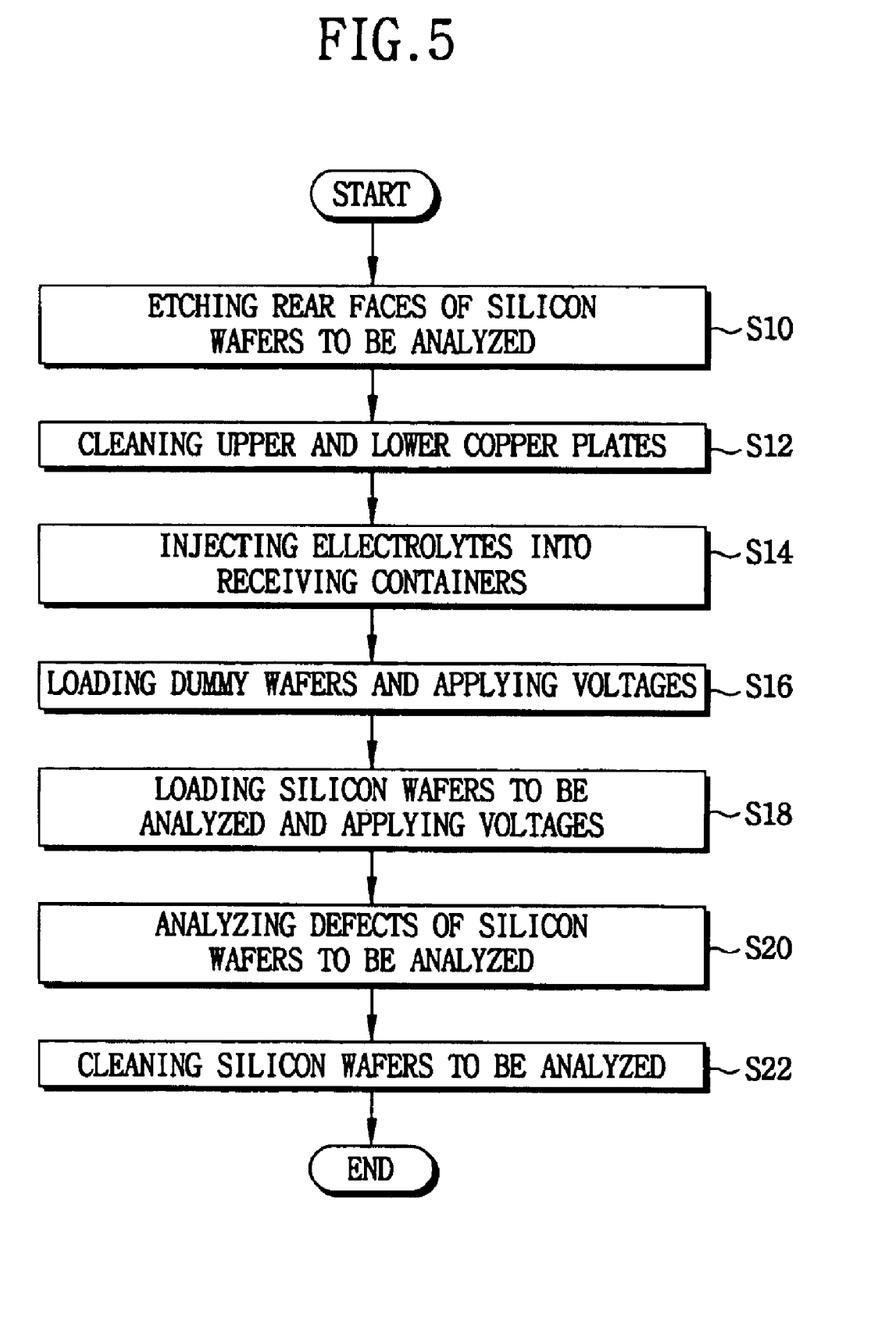
FIG. 5 is a flow chart illustrating a method for analyzing silicon wafers employing a copper decoration according to an embodiment of the present invention.

FIG. 5 is a flow chart illustrating a method for analyzing silicon wafers employing a copper decoration according to an embodiment of the present invention.

Referring to FIGS. 3–5, rear faces of silicon wafers W to be analyzed are etched (step S10). By the etching of step S10, native oxide films formed on the rear faces of the silicon wafers W are removed and thus, rear faces of the silicon wafers W to be analyzed have respective electrical conductivities. An oxide film having a thickness of about 400 to about 1,200 Å is formed on the silicon wafer W to be analyzed before the etching of step S10. When the apparatus for analyzing a substrate using a copper decoration of the present invention is employed to analyze the silicon wafers W, several silicon wafers W may be simultaneously analyzed because the apparatus for analyzing a substrate may include several receiving containers 104. Thus, the etching process of step S10 is performed for a number of silicon wafers W to be analyzed that corresponds to a number of receiving containers 104 provided in the apparatus for analyzing a substrate.

Upper copper plates 112 and lower copper plates 110 installed in the receiving containers 104 are cleaned (step S12).

Electrolytes 102 are respectively injected into the receiving containers 104 (step S14).

After dummy wafers are respectively loaded into the receiving containers 104 having the electrolytes 102 injected therein, voltages are applied from power source 114 to the lower copper plates 110 and the upper copper plates 112 (step S16). Thus, electric fields are respectively generated between the upper copper plates 112 and the lower copper plates 110, and copper ions provided from the upper copper plates 112 are dissolved in the electrolytes 102. To sufficiently dissolve the copper ions in the electrolytes 102, the above-described process is performed for a relatively long period of time of about 30 minutes to about 1 hour. An oxide film having a thickness of about 1,000 Å is formed on an upper face of each dummy wafer loaded in the receiving container 104. In this case, the voltages provided from the power source 114 are selectively applied to some upper copper plates 112 and some lower copper plates 110 installed in some of the receiving containers 104 in which the silicon wafers W to be analyzed are directly loaded and analyzed.

When the copper ions are sufficiently dissolved in the electrolytes 102, the silicon wafers W to be analyzed are loaded into the receiving containers 104 after the dummy wafers are unloaded therefrom (step S18).

Subsequently, voltages are applied from the power source 114 to the upper and lower copper plates 112 and 110, so that the copper ions in the electrolytes 102 are decorated at defected portions of the silicon wafers W to be analyzed (step S20).

Silicon oxide films are respectively formed on the silicon wafers W to be analyzed. However, a portion of the silicon oxide film formed at a portion of the silicon wafer W having a crystalline defect has a thickness that is relatively thinner than that of other portions of the silicon oxide film positioned at portions of the silicon wafer W not having crystalline defects. Hence, when negative bias voltage is applied to the lower copper plate 110 from the power source 114, the thin portion of the silicon oxide positioned at the portion of the silicon wafer W having the crystalline defect is broken down, and the copper cations in the electrolyte 102 are reduced, thereby depositing the copper at the portion of the silicon wafer W having the crystalline defect. Then, the copper diffuses into a bulk of the silicon wafer W so that copper extractions are decorated. The crystalline defect of the silicon wafer W is analyzed in accordance with a distribution and a density of copper decorations thus produced.

Then, the silicon wafers W to be analyzed are cleaned (step S22).

According to the above-described method for analyzing the silicon wafers W, a plurality of silicon wafers W may be simultaneously analyzed using one apparatus for analyzing a substrate. Hence, a time required for analyzing the silicon wafers W may be greatly reduced. In the conventional method for analyzing silicon wafers, because preparation processes for analyzing a silicon wafer should be performed just prior to analysis for every silicon wafer, a time for analyzing a plurality of silicon wafers may be greatly increased, and the method for analyzing the silicon wafers may be complicated. However, according to the present method, a plurality of silicon wafers W may be analyzed through one preparation process.

Embodiment 2

Figure 6:
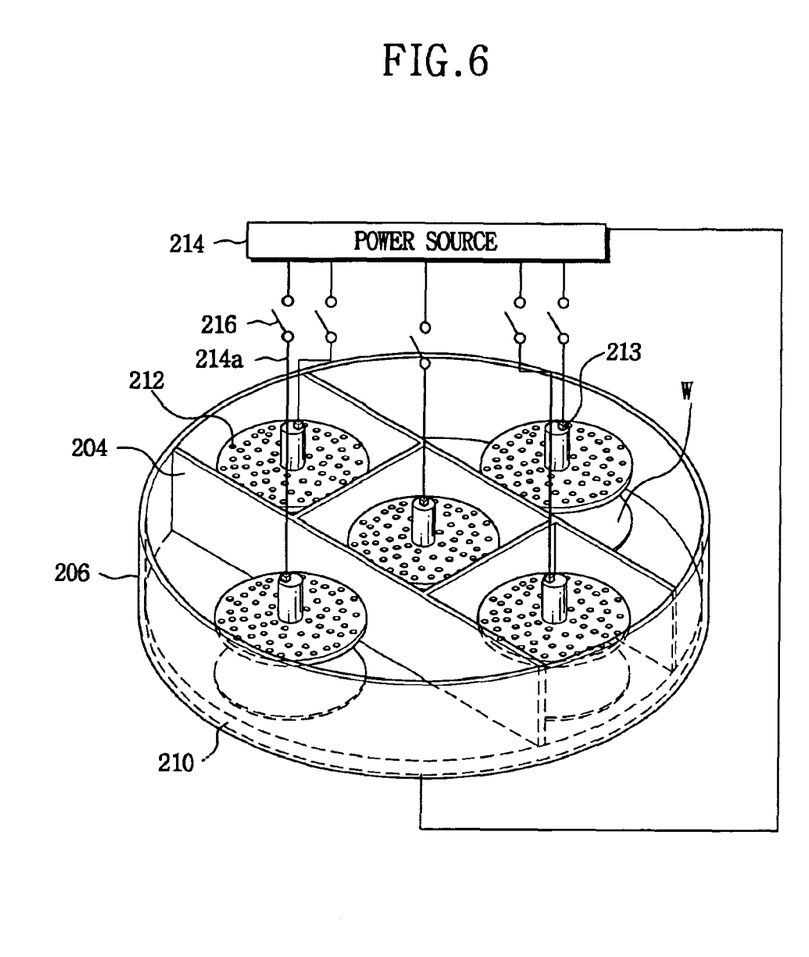
FIG. 6 illustrates a schematic perspective view illustrating an apparatus for analyzing a substrate according to another embodiment of the present invention.

FIG. 6 illustrates a schematic perspective view of an apparatus for analyzing a substrate according to a second embodiment of the present invention.

Referring to FIG. 6, an apparatus for analyzing a substrate of the present embodiment has a bath 206 including at least two receiving containers 204 that independently receive electrolytes. The receiving containers 204 are defined by isolation walls provided in the bath 206. The receiving containers 204 defined by the isolation walls have sufficient dimensions so that rear faces of silicon wafers W to be analyzed are adequately positioned on bottom faces of the receiving containers 204, respectively. Hereinafter, the receiving containers 204 provided in the bath 206 will be referred to as first to N-th receiving containers 204.

A lower copper plate 210 is provided on an entire bottom face of the bath 206. The rear faces of the silicon wafers W to be analyzed are placed on an upper face of the lower copper plate 210. The lower copper plate 210 is divided into a plurality of portions defined by the receiving containers 204. The divided portions of the lower copper plate 210 have sufficient sizes at which the rear faces of the silicon wafers W to be analyzed are adequately positioned. Thus, one silicon wafer W to be analyzed is placed at one portion of the lower copper plate 210 defined by one receiving container 204.

First to N-th upper copper plates 212 are provided in the first to N-th receiving containers 204, respectively. Each of the upper copper plates 212 corresponds to the lower copper plate 210 by a predetermined interval. In addition, the first to N-th upper copper plates 212 respectively correspond to front faces of the silicon wafers W to be analyzed loaded at the portions of the lower copper plate 210 defined by the receiving containers 204. The intervals between the upper copper plates 212 and the lower copper plate 210 are adequately maintained to sufficiently separate the upper copper plates 212 from the silicon wafers W loaded at the portion of the lower plate 210. Though not shown in the figure, supporting members may be installed in the receiving containers 204 to support the upper copper plates 212.

The lower copper plate 210 and the first to N-th upper copper plates 212 respectively include connecting terminals 213 connected to a power source 214.

In the present embodiment, the apparatus for analyzing a substrate has one power source 214. The power source 214 includes power cables 214a connected to a negative terminal and a positive terminal of the power source 214. Some power cables 214a connected to the positive terminal of the power source 214 are extended to the first to N-th upper copper plates 212, respectively. Additionally, other power cables 214a connected to the negative terminal of the power source 214 are extended to the lower copper plate 210. First to N-th upper switching devices 216 are provided between power cables 214a and the first to N-th upper copper plates 212, respectively. Hence, voltages may be selectively applied to desired upper copper plates 212 from the power source 214 in accordance with selective ON/OFF operations of the first to N-th upper switching devices 216.

Because the lower copper plate 210 is formed on the entire bottom face of the bath 206, the voltages are not selectively applied to the lower copper plate. However, the voltages may be selectively applied to the upper copper plates 212 because the upper copper plates 212 are provided in the receiving containers 204. Therefore, electric fields may be selectively generated between the lower copper plate 210 and selected upper copper plates 212 by selectively applying the voltages to the selected upper copper plates 212 provided in the receiving containers 204 where the silicon wafers W to be analyzed are positioned.

Embodiment 3

Figure 7:
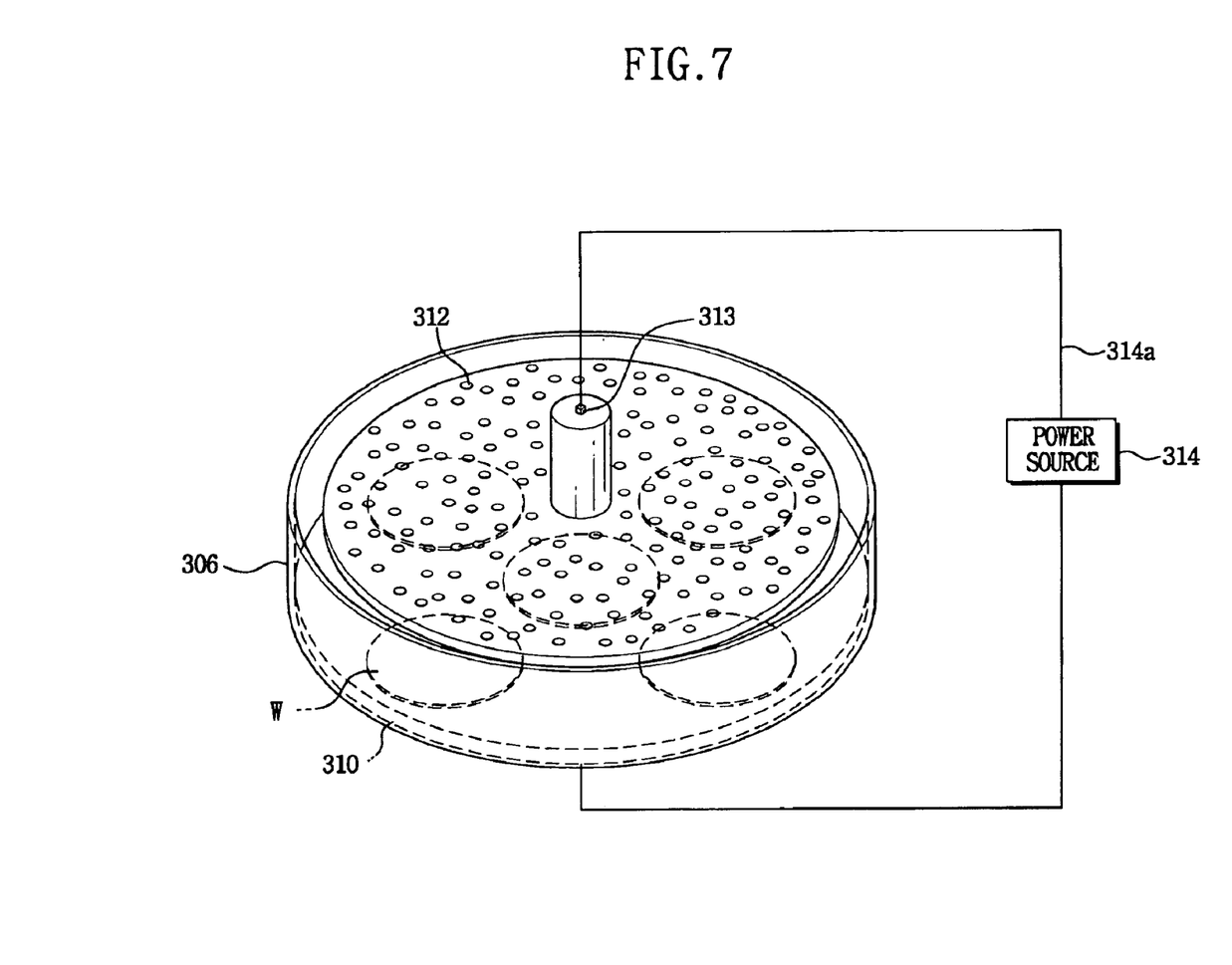
FIG. 7 illustrates a schematic perspective view illustrating an apparatus for analyzing a substrate according to still another embodiment of the present invention.

FIG. 7 illustrates a schematic perspective view of an apparatus for analyzing a substrate according to a third embodiment of the present invention.

Referring to FIG. 7, an apparatus for analyzing a substrate has a bath 306 for receiving an electrolyte. The bath 306 has a size that at least two rear faces of silicon wafers W to be analyzed are received on a bottom face thereof.

A lower copper plate 310 is provided on an entire bottom face of the bath 306. Thus, at least two rear faces of the silicon wafers W to be analyzed are positioned on an upper face of the lower copper plate 310. An upper copper plate 312 is provided to correspond to the lower copper plate 310. The upper copper plate 312 has a size substantially identical to that of the lower copper plate 310.

The apparatus of the present embodiment has a power source 314 for providing voltages to the upper and lower copper plates 312 and 310. The upper and lower copper plates 312 and 310 respectively have connecting terminals 313 connected to a power source 314. The power source 314 includes power cables 314a connected to a positive terminal and a negative terminal thereof. The power cables 314a connected to the positive terminal of the power source 314 are connected to the upper copper plates 312, respectively. Also, the power cables 314a connected to the negative terminal of the power source 314 are connected to the lower copper plate 310.

With the above-described apparatus for analyzing a substrate, at least two silicon wafers W may be simultaneously analyzed after the silicon wafers W to be analyzed are loaded. Thus, an amount of time necessary for analyzing the silicon wafers W may be greatly reduced.

According to the present invention, a plurality of silicon wafers may be simultaneously analyzed using one apparatus for analyzing a substrate, thereby substantially reducing an amount of time required for analyzing the silicon wafers. Additionally, a method for analyzing silicon wafers may be simplified because a plurality of silicon wafers may be simultaneously analyzed through one preparation process.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. An apparatus for analyzing a substrate employing a copper decoration, the apparatus comprising:
   a bath having at least two receiving containers for receiving electrolytes;
   slots formed at insides of the receiving containers for receiving substrates to be analyzed in a direction that is normal to a bottom face of the bath;
   lower copper plates provided in the receiving containers, the lower copper plates making contact with entire rear faces of the substrates received in the receiving containers;
   upper copper plates provided in the receiving containers, each of the upper copper plates corresponding to a respective one of the lower copper plates, and separated from front faces of the substrates; and
   a power source connected to the upper copper plates and to the lower copper plates for providing voltages to the upper copper plates and to the lower copper plates.

2. The apparatus as claimed in claim 1, wherein the receiving containers are separated from each other to prevent the electrolytes received in the receiving containers from being mixed together.

3. The apparatus as claimed in claim 1, wherein the upper copper plates and the lower copper plates provided in the receiving containers are connected to the power source in parallel.

4. The apparatus as claimed in claim 3, further comprising first switching devices provided between the power source and the lower copper plates in order to selectively apply the voltages to the lower copper plates from the power source.

5. The apparatus as claimed in claim 3, further comprising second switching devices provided between the power source and the upper copper plates in order to selectively apply the voltages to the upper copper plates from the power source.

6. The apparatus as claimed in claim 1, further comprising additional power sources corresponding to the number of the receiving containers, and the upper copper plates and the lower copper plates are connected to each of the power sources in series.

7. The apparatus as claimed in claim 1, wherein the power source has a negative bias terminal connected to the lower copper plates, and a positive bias terminal connected to the upper copper plates.

8. The apparatus as claimed in claim 1, wherein the lower copper plates have connecting terminals connected to the power source.

9. The apparatus as claimed in claim 1, wherein the upper copper plates have connecting terminals connected to the power source.

10. The apparatus as claimed in claim 1, wherein the electrolyte includes methanol.

11. The apparatus as claimed in claim 1, wherein the receiving containers have predetermined depths to completely receive the substrates in the direction that is normal to the bottom face of the bath.

12. An apparatus for analyzing a substrate employing a copper decoration, comprising:
   a bath having at least two receiving containers defined by isolation walls wherein the receiving containers independently receive electrolytes, respectively;

a lower copper plate provided on an entire bottom face of the bath;

upper copper plates provided in the receiving containers, the upper copper plates corresponding to the lower copper plate and being separated from the lower copper plate; and a power source connected to the upper copper plates and to the lower copper plate for providing voltages to the upper copper plates and to the lower copper plate.

13. The apparatus as claimed in claim 12, wherein the receiving containers define portions of the lower copper plate so that the portions of the lower copper plate defined by the receiving containers have respective sizes sufficient to receive rear faces of substrates to be analyzed.

14. The apparatus as claimed in claim 12, further comprising switching devices provided between the power source and the upper copper plates in order to selectively apply the voltages to the upper copper plates from the power source.

15. The apparatus as claimed in claim 12, wherein the lower copper plate includes a connecting terminal connected to the power source.

16. The apparatus as claimed in claim 12, wherein the upper copper plates include connecting terminals connected to the power source.

17. The apparatus as claimed in claim 12, wherein the power source includes a negative bias terminal connected to the lower copper plate, and a positive bias terminal connected to the upper copper plates.

18. An apparatus for analyzing a substrate employing a copper decoration, comprising:

a bath including a bottom face for receiving at least two substrates to be analyzed, wherein an electrolyte is received in the bath;

a lower copper plate provided on an entire bottom face of the bath wherein the substrates to be analyzed are placed on an upper face of the lower copper plate;

an upper copper plate provided in the bath, the upper copper plate corresponding to the lower copper plate and being separated from the lower copper plate; and a power source for providing voltages to the upper copper plate and to the lower copper plate.

19. The apparatus as claimed in claim 18, wherein the power source includes a negative bias terminal connected to the lower copper plate, and a positive bias terminal connected to the upper copper plate.

* * * * *